United States Patent [19]

Shen

[11] Patent Number: 5,221,961

[45] Date of Patent: Jun. 22, 1993

[54] STRUCTURE OF BIAXIAL PHOTOMETER

[76] Inventor: Thomas Y. Shen, 63-2, Cheng Kong Road, Sec. 1, Nan Kung Area, Taipei, Taiwan

[21] Appl. No.: 842,641

[22] Filed: Feb. 27, 1992

[51] Int. Cl.$^5$ .............................................. G01N 21/59
[52] U.S. Cl. ..................................... 356/432; 356/440
[58] Field of Search ............... 356/432, 433, 434, 435, 356/436, 440; 250/573

[56] References Cited

U.S. PATENT DOCUMENTS

| | | | |
|---|---|---|---|
| 3,995,960 | 12/1976 | Fletcher et al. | 356/433 |
| 4,038,982 | 8/1977 | Burke et al. | 250/573 |
| 4,041,502 | 9/1977 | Williams et al. | 250/573 |
| 5,146,294 | 9/1992 | Grisar et al. | 356/435 |

Primary Examiner—Richard A. Rosenberger
Attorney, Agent, or Firm—Varndell Legal Group

[57] ABSTRACT

A biaxial photometer, comprising a mainframe having an optical system secured thereto at one end by a rotary shaft for holding a horizontal sample holder when it is rotated to a horizontal position, or a vertical sample holder when it is rotated to a vertical position. Sample test tube can be inserted in the horizontal sample holder or the vertical sample holder and disposed in a horizontal or vertical position in the passage of the light beam emitted from the optical system for making an assay horizontally or vertically as desired.

3 Claims, 3 Drawing Sheets

STRUCTURE OF BIAXIAL PHOTOMETER

BACKGROUND OF THE INVENTION

The present invention relates to photometers, and more particularly to a structure of biaxial photometer which can be conveniently converted for measuring the emitting light intensity (transmittance) from test solution either horizontaally or vertically.

Photometer is an instrument used in measuring the intensity of light, esp. in determining the intensity of emitting light (transmittance) from different samples relative to a standard. Presently, for determine the transmittance of light from solution sample, there are two different types of photometers available, one with the light source travvels vertically i.e. from top to bottom (or bottom to top) of the test sample, such as microplate reader, and the other is the more conventional photometer which the light source travels through the test sample horizontally, such as spectrophotometer. Two different types of photometers are generally required in most laboratories for various tests.

SUMMARY OF THE INVENTION

The present invention has been accomplished under the circumstances in view. It is therefore the main object of the present invention to provide a biaxial photometer which can be conveniently converted from on position to another for measuring the transmittance of test samples either horizontally or vertically.

BRIEF DESCRIPTION OF THE DRAWINGS

The present invention will now be described by way of example only, with reference to the annexed drawings, in which.

DETAILED DESCRIPTION OF THE PREFERRED EMBODIMENT

Figure 1:
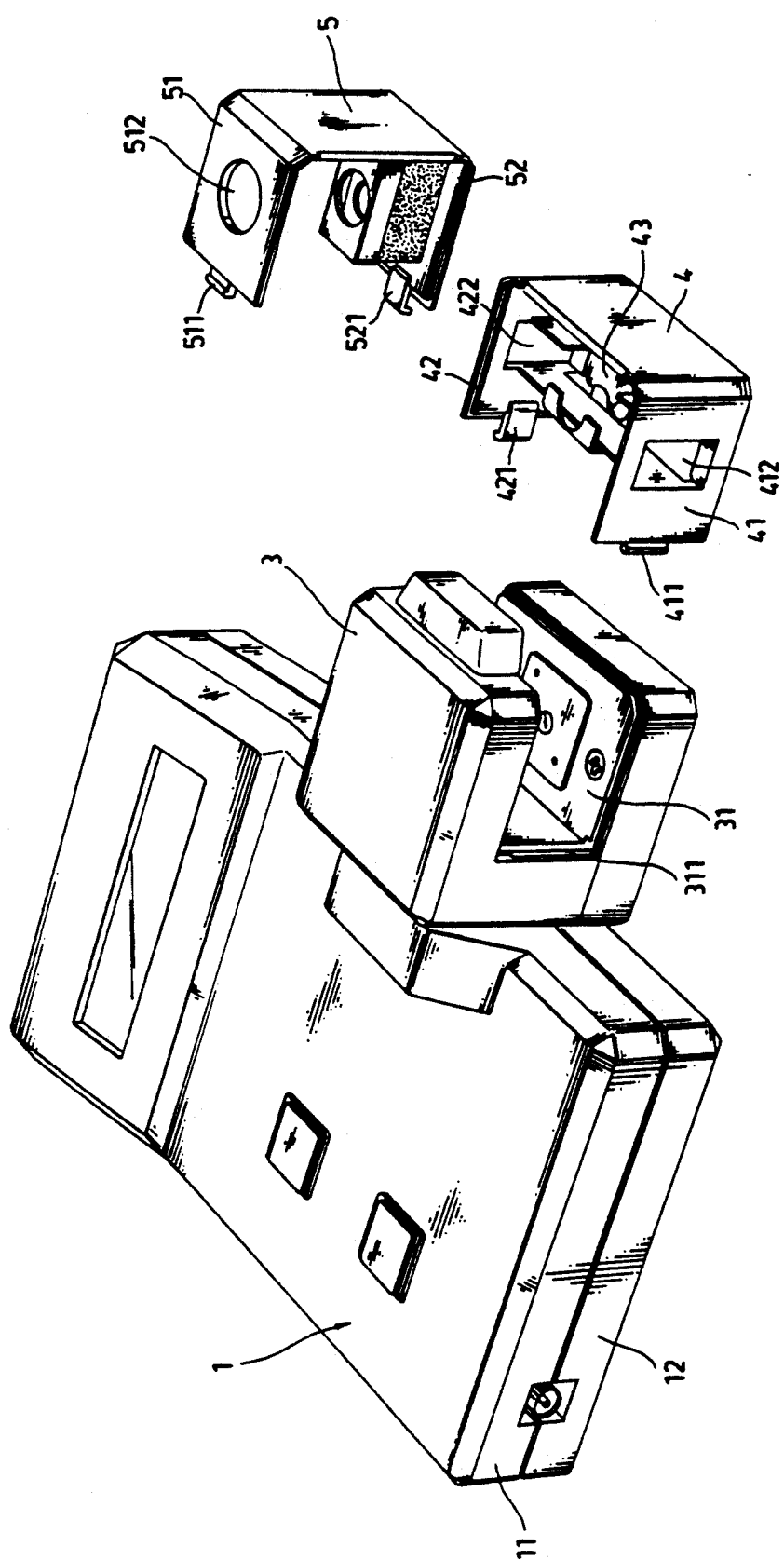
FIG. 1 is a perspective assembly view of the preferred embodiment of the present invention.
Figure 2:
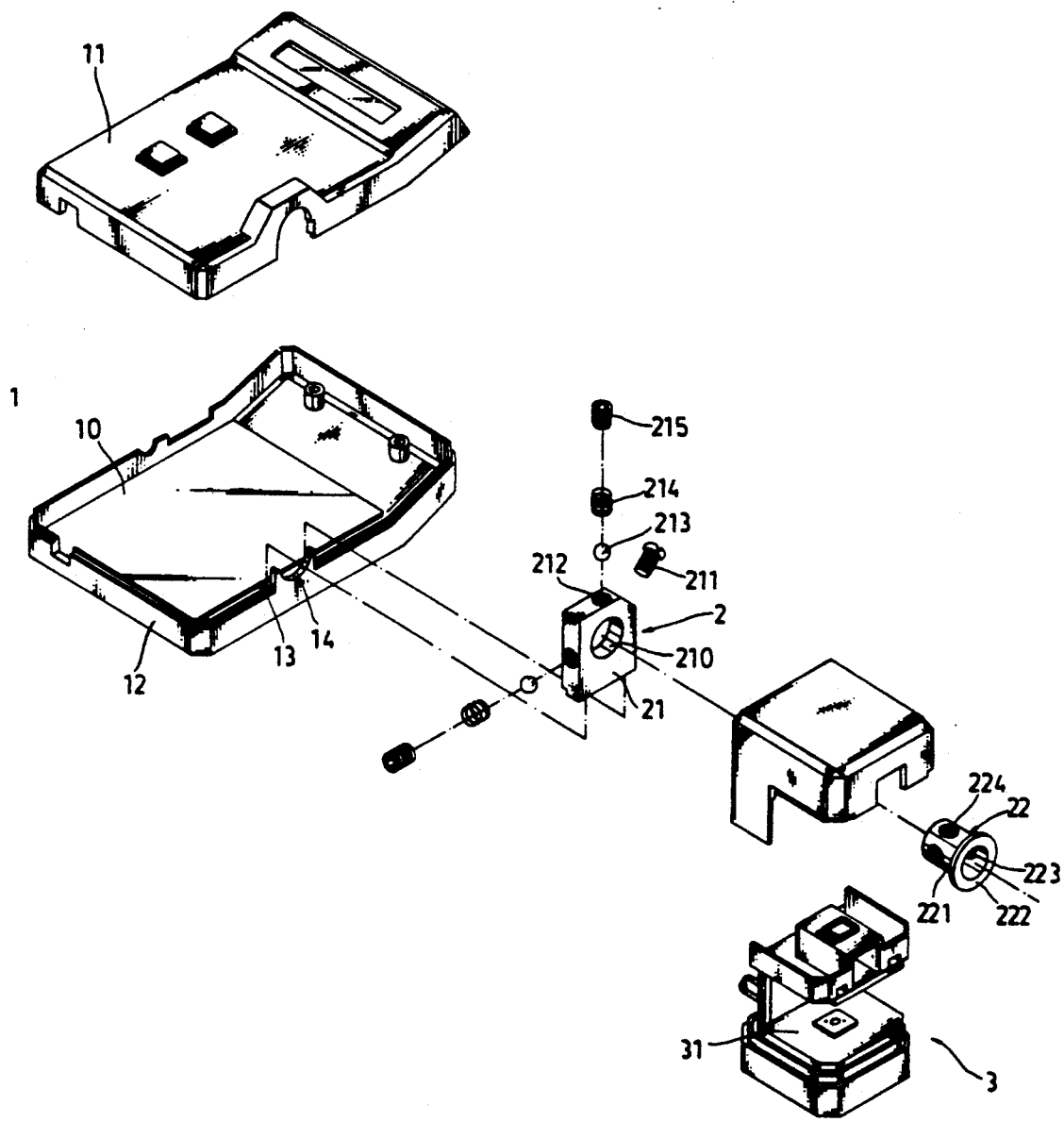
FIG. 2 is a perspective dismantled view thereof.

Referring to FIGS. 1 and 2, a biaxial photometer in accordance with the present invention is generally comprised of a mainframe 1, a rotary shaft 2, an optical system 3, a horizontal sample holder 4, and a vertical sample holder 5. The mainframe 1 is comprised of an upper shell 11 and a bottom shell 12, having received a measuring circuit 10 received therein, a hole 14 made thereon laterally at one side. The bottom shell 12 of the mainframe 1 has a mounting seat 13 for mounting a bearing block 21 which is provided for holding the rotary shaft 2 in place. The rotary shaft 2 is generally comprised of a bearing block 21 which is fastened in the mounting seat 13 of the mainframe 1, and a cylinder 22 which is fastened in said bearing block 21. The bearing block 21 has an axial hole 210 at the center for mounting the cylinder 22, a stop bolt 211 fastened therein at one side and normally projecting in said axial hole 210 (see FIG. 3), two side holes 212 respectively spaced from each other at 90 angle and disposed in communication with said axial hole 210 of which each has fastened therein a steel ball 213 retained by a spring 214 and a screw bolt 215. By adjusting the screw bolt 215, the steel ball 213 in each side hole 212 can be pushed toward the axial hole 210. The cylinder 22 has a flange 222 at one end of the body 221 and made in outer diameter relatively larger than the outer diameter of the body 221. The body 221 of the cylinder 22 is inserted in the axial hole 210 of the bearing block 21, having radially made thereon an elongated slot 223 in length suitable for rotation through 90° angle relative to the stop bolt 211 and in width slightly larger than the diameter of the stop bolt 211, and two locating holes 224 (in diameter slightly smaller than the steel ball 213 in each side hole 212) corresponding to the two side holes 212 of the bearing block 21. Because the stop bolt 211 is fastened in the bearing block 21 and projecting in the elongated slot 223 of the cylinder 22, the cylinder is permitted to rotate in the axial hole 210 within 90° angle. During assembly, the cylinder 2 is inserted through the optical system 3 into the bearing block 21 with its flange 222 fixedly secured to the optical system 3 by fastening elements. Therefore, the optical system 3 can be rotated within 90° angle relative to the mainframe 1, i.e. the effective measuring space 31 in the optical system 3 can be adjusted to a horizontal or vertical position for mounting the horizontal sample holder 4 or the vertical sample holder 5. The horizontal sample holder 4 and the vertical sample holder 5 are respectively designed in a substantially U-shaped structure, having each two hooked strips 411,421 or 511,521 respectively projecting from the two opposite side walls 41, 42 or 51,52 thereof and engaged in two opposite grooves 311 inside the measuring space 31 of the optical system 3. The two opposite side walls 41,42 of the horizontal sample holder 4 have each a through-hole 412 or 412 aligned with each other axially, through which a test tube can be inserted to the light beam passage 43 for assay. The vertical sample holder 5 has a through-hole 512 in geometric shape (for example, in round or square shape) on the upper side wall 51 thereof for mounting a test tube, permitting a test tube to be vertically disposed in the way through which the light beam from the optical system 3 passes.

Figure 3:
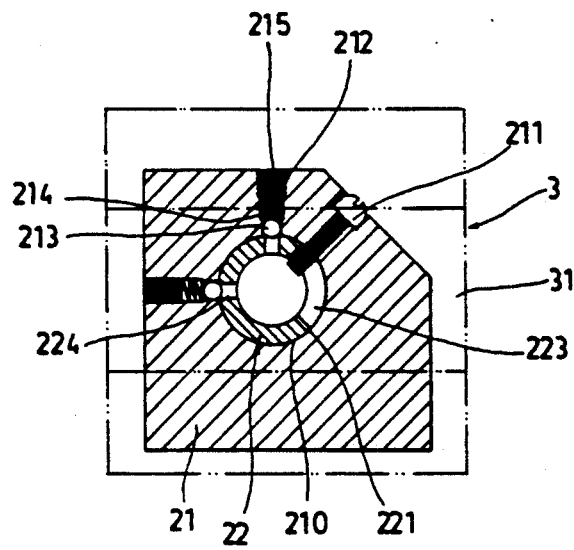
FIG. 3 is a schematic drawing of the present invention under the status of doing an assay horizontally.
Figure 4:
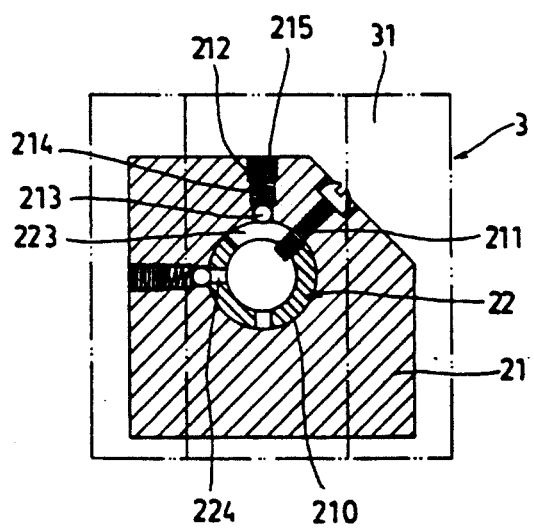
FIG. 4 is a schematic drawing of the present invention under the status of doing an assay vertically.

Referring to FIGS. 3 and 4, the horizontal sample holder 4 and the vertical sample holder 5 can be alternatively attached to the optical system 3 for different assay procedure. In FIG. 3, the optical system 3 is disposed at a horizontal position for mounting the horizontal sample holder 4. When vertical test procedure is required, the optical system 3 is rotated through 90° angle relative to the mainframe 1, permitting the steel ball 213 in each side hole 212 of the bearing block 21 to be engaged from one locating hole 224 in another, and simultaneously permitting the stop bolt 211 to be disposed from one end in the elongated slot 223 to the opposite end (see FIG. 4). Thus, the optical system 3 is rotated to a vertical position for mounting the vertical sample holder 5 for performing vertical test procedure.

I claim:

1. A biaxial photometer, comprised of a mainframe, a rotary shaft, an optical system, a horizontal sample holder and a vertical sample holder, said mainframe comprised of an upper shell and a bottom shell with a measuring circuit received therein, said bottom shell having a mounting seat and a hole laterally made at one side for mounting said rotary shaft to rotatably secure said optical system thereto in a horizontal or vertical position, and characterized in that:

said rotary shaft comprises a bearing block fastened in said mounting seat of said bottom shell of said mainframe, and a cylinder, said bearing block having an axial hole at the center for mounting said cylinder, a stop bolt fastened at one side and normally projecting in said axial hole, a plurality of side holes respectively spaced from one another at 90° angle interval and disposed in communication with said axial hole, said side holes having each a steel ball fastened therein and retained by a spring and a screw bolt, said cylinder having one end fixedly secured to said optical system, an elongated slot radially made thereon for insertion therein of said stop bolt, and a plurality of locating holes corresponding to said side holes of said bearing block for alternative positioning of said steel ball; said horizontal and vertical sample holders are respectively designed in a substantially U-shaped structure, having each two hooked strips respectively projecting from the two opposite ends thereof for engaging in two opposite grooves made inside said optical system, permitting the test tube inserted in said horizontal or vertical sample holder to be alternatively disposed in a horizontal or vertical position in the passage of the light beam emitted from said optical system.

2. The biaxial photometer of claim 1, wherein said elongated slot on said cylinder is made in such a length that said stop bolt is stopped at one end of said elongated slot when said optical system is disposed in a horizontal position, or stopped at the opposite end of said elongated when said optical system is disposed in a vertical position, and made in width slightly larger than the diameter of the stop bolt.

3. The biaxial photometer of claim 1, wherein said locating holes of said cylinder have each an inner diameter slightly smaller than the outer diameter of said steel ball.

* * * * *